United States Patent
Company et al.

(10) Patent No.: US 8,142,525 B2
(45) Date of Patent: Mar. 27, 2012

(54) PREPARATION OF FATTY ACID ESTERS OF GLYCEROL FORMAL AND ITS USE AS BIOFUEL

(75) Inventors: Carles Estevez Company, Sitges (ES); Natividad Bayarri Ferrer, Badalona (ES); Josep Castells Boliart, Montmelo (ES)

(73) Assignee: Institut Univ. De Ciencia I Tecnologia, S.A., Barcelona (ES)

( * ) Notice: Subject to any disclaimer, the term of this patent is extended or adjusted under 35 U.S.C. 154(b) by 450 days.

(21) Appl. No.: 12/373,175

(22) PCT Filed: Jul. 11, 2007

(86) PCT No.: PCT/EP2007/057123
§ 371 (c)(1),
(2), (4) Date: Jul. 31, 2009

(87) PCT Pub. No.: WO2008/006860
PCT Pub. Date: Jan. 17, 2008

(65) Prior Publication Data
US 2010/0005708 A1    Jan. 14, 2010

(30) Foreign Application Priority Data
Jul. 13, 2006   (ES) .................................. 200601918

(51) Int. Cl.
*C10L 1/18* (2006.01)
(52) U.S. Cl. ................. 44/349; 44/350; 44/388; 44/400
(58) Field of Classification Search .................... 44/349, 44/350, 388, 400
See application file for complete search history.

(56) References Cited

U.S. PATENT DOCUMENTS
5,578,090 A * 11/1996 Bradin ............................ 44/308
6,586,465 B1   7/2003 Imperante et al. ............ 514/452

FOREIGN PATENT DOCUMENTS
| | | |
|---|---|---|
| EP | 1 331 260 | 7/2003 |
| JP | 2002-069068 | 3/2002 |
| WO | WO 2006/084048 | 8/2006 |

OTHER PUBLICATIONS
Imanaka, T; Nagumo, H; Tanaka, T; Tawara, H: "Preparation of monoglyceride ketals useful for emulsifiers, foam bulking agents and plastic additives, comprises the reaction of fats and ketones or aldehydes:", Derwent Publications Ltd., London, Accession No. 2002-430038 corresponding to JP 2002-069068 Published Mar. 8, 2002.
Wessendorf, R: "Glycerinderivative als kraftsoffkomponenten" Erdoel Erdgas Kohle, Urban verlag, Hamburg De, vol. 48, No. 3, Mar. 1, 1995, pp. 138-148.
PCT International Search Report for WO 2008/006860 A3, mailed Mar. 25, 2008.

* cited by examiner

*Primary Examiner* — Cephia D Toomer
(74) *Attorney, Agent, or Firm* — Locke Lord LLP

(57) ABSTRACT

This invention describes the preparation of fatty acid esters of glycerol formal either by a triglyceride transesterification process or, alternatively, by an esterification process of fatty acids previously obtained from the hydrolysis of triglycerides (fat splitting), with glycerol formal in the presence of an acid or basic catalyst. Also the invention describes the use of these fatty acid esters of glycerol formal prepared by said process as biofuel. In an embodiment, such biofuel is used in the preparation of other biofuels by its mixture with a product selected from a group formed by: glycerol formal, biodiesel, petrol-derived diesel, and mixtures thereof. The biofuels thus obtained are characterized to allow the complete incorporation of the glycerol obtained in the current biodiesel production process in a biodiesel fuel.

8 Claims, No Drawings

PREPARATION OF FATTY ACID ESTERS OF GLYCEROL FORMAL AND ITS USE AS BIOFUEL

This application is a national phase entry under 35 U.S.C. §371 of International Application No. PCT/EP2007/057123, filed Jul. 11, 2007, hereby incorporated by reference, which itself claims priority to Spanish Patent Application No. P 200601918, filed Jul. 13, 2006, hereby incorporated by reference.

BACKGROUND ART

The growing production of biofuel, particularly of biodiesel, as alternative to the use of petrol based biofuels is based in two basic needs of the socioeconomic model in the industrialised countries. On one hand, the reduction of the petrol dependency whose prize has been significantly increased during the last years and with a predicted growing tendency. On the other hand, the reduction of emissions associated with the diesel combustion in vehicles engines, with special emphasis in CO, $CO_2$, $SO_x$ and particles, which has been proved to be reduced in the case of biodiesel use, although the $NO_x$ level are still high.

The current biodiesel process is based in a transesterification of vegetable and based triglycerides with methanol or ethanol to obtain fatty acid methyl or ethyl esters (biodiesel) and glycerol (concomitant byproduct in the transesterification reaction) obtaining approximately 100 tones of glycerol pre 1.000 tones of biodiesel. If in 2005 the European objectives of the substitution of 2% of petrol based diesel for biodiesel were accomplished, Europe would have been produced 400.000 tones of glycerol per year, that is, approximately double the needs of the current European glycerol market. This high annual production of glycerol represents one of the most important inconveniences in the biodiesel manufacture, which could affect negatively in the development of the biodiesel market.

It is necessary, therefore, to develop new high market application for the produced glycerol in the biodiesel manufacturing. It has been recently proposed a cheap transformation of glycerol in substances to be mixed with alkyl fatty acid esters ready to act as a biofuel. This solution could be of high technical and commercial value and it will solve the problems derived from the excess of glycerol.

For example, the patent filed WO 2005/093015 A1 described the preparation of two glycerol acetals through the reaction of glycerol and n-butanal and acetone. It is also described the preparation of glycerol t-butylethers through the reaction of crude glycerol and isobutylene. In both cases the glycerol used was crude glycerol as byproduct in the biodiesel manufacturing from the transesterification process of rapeseed oil with methanol in the presence of zinc aluminate as a heterogeneous catalyst. It is reported that both ethers and acetals described are mixed in an 80/20 p/p (biodiesel/glycerol derivative), ensuring, then, the total utilisation of glycerol as biofuel. However, the low temperature miscibility is not reported, therefore, is not possible to evaluate the behaviour as biofuel at low temperature, an important aspect to determine the general use of biofuels in cold climates.

The European patent filed EP 1331260 A2 described a procedure to produce biodiesel fuels with improved properties at low temperature. In this case the crude glycerol obtained in the preparation of biodiesel is reacted, after its neutralisation with $H_2SO_4$ to pH 7, with aldehydes and ketones through known procedures to obtain acetals and ketals. The properties at low temperature of methyl esters of rapeseed oil and glycerol formal and with glycerol triacetate is described in weight proportions from 95.5/0.5 to 90/10 (biodiesel/glycerol derivative). The data reported showed that the addition of glycerol formal derivative into the biodiesel produced a maximum freeze point reduction (−21° C.) and of viscosity at −10° C. (343.3 cST of a 95/5 mixture). In the light of this result it seems that glycerol formal constitute one of the most efficient alternative to warrantee the best properties of biodiesel at low temperature. Although the author indicates that the concentration of acetals, ketals and glycerol acetate may vary between 0.1 and 20% weight depending of the needs, it is not indicated is it is possible to prepared mixtures of glycerol formal and biodiesel when the amount of glycerol formal is high of 5%. The data obtain in our laboratory shows that the glycerol formal is immiscible with fatty acid based methyl esters derived from vegetable oils such as rapeseed, sunflower or palm oil, when the proportion of glycerol formal is 20% at the temperatures ranges between −20 and +25° C., excluding, then, glycerol formal as a component of biodiesel fuel formulation, allowing the complete incorporation of glycerol.

On the other hand, the literature studied (e.g. the article "Glycerinderivate als Kraftstoffkomponenten", R. Wessendorf, Erdöl und Kohle-Erdgas, 48, 3, 1995) does not contemplate the associated cost in the use of aldehydes, ketones, olefins and other chemical products needed for the synthesis of the proposed glycerol derivatives. Form the economical point of view, glycerol formal is a suitable material for the preparation of biofuel since its industrial availability and its prize may be competitive enough.

Finally, from the strategic point of view it is convenient to base the chemical production in Europe in the use of renewable materials or from natural gas, minimising the use of petrol derivatives (Strategic Research Agenda. Technology Platform of Sustainable Chemistry). This vision is not only to be taking into account in the production of biofuels only but also is adopted as a general directive. With all this data on hand, is it possible to conclude that glycerol formal is the most suitable glycerol derivative since the starting material needed for its production, formaldehyde, is prepared from methanol, which is obtained from the oxidation of natural gas.

DESCRIPTION OF THE INVENTION

This invention relates to the preparation of new biofuels which include in its composition glycerol formal (obtained by acetalisation of glycerol with formaldehyde), in such a way that it is possible to use the total amount of glycerol obtained as by-product in the current process of manufacturing biodiesel.

The present invention provides an optimum solution from the point of view technical, economical, and strategic to the glycerol overstock problem. It is based on the use of glycerol formal for the preparation of biofuels whose composition allows to incorporate a concentration of glycerol equal or higher than 20% w/w, keeping the good properties of the biofuels for engines, specially at low temperature.

Therefore, an aspect of the present invention refers to the preparation of a biofuel with a global content of the components (I) and (II) equal or higher than 85% w/w,

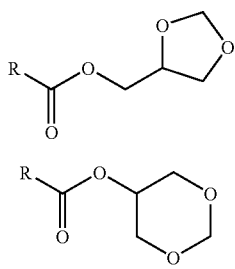

where R is an alkyl chain of a fatty acid, which includes the following steps: where R is an alkyl chain from a fatty acid, which comprises the following steps: (a) carrying out a transesterification reaction between the triglycerides of an oil or fat of animal or vegetable origin, and glycerol formal, in the presence of an acid or base; (b) removing the lower layer from the upper layer which is the biofuel; and (c) optionally washing the biofuel obtained in the step (b) with water, and drying. An alternative process involves, submitting the triglycerides of an oil or fat of animal or vegetable origin to a hydrolysis process (commonly named fat splitting) to generate the fatty acids and glycerol, followed by an esterification process of the fatty acids obtained with glycerol formal, in the presence of an acid or base catalyst.

The transesterification of triglycerides, of animal or vegetable origin, with glycerol formal gives glycerol formal monoesters of fatty acids with yields equal or higher than 85%. The glycerol formal esters consist of a mixture of isomers (I) and (II), where R is the alkyl chain of the fatty acids. Preferably, the catalysts are selected from the group comprising basic homogeneous catalysts, including alkali metal hydroxides, more preferably potassium hydroxide; alkali metal alkoxides; solid acid-base catalysts, including heterogeneous catalysts, and ion exchange resins. In a preferred embodiment, the biofuel has a content in the compounds (I) and (II) higher than 95%.

According to the invention, the triglycerides from oil and fat can be from any animal or vegetable source, for example, rapeseed, sunflower, coconut, soy, or olive or mixtures thereof. In a preferred embodiment, the rapeseed oil is used.

Glycerol formal can be obtained from crude glycerol by an acetalisation process to yield a product with a purity higher than 98%. The transformation of crude glycerol into glycerol formal with a purity higher than 98% may be carried out by any known process such as the one described, for instance, in the patent DE 196 48960, using heterogeneous catalysts which allow to obtain a water- and salt-free glycerol crude, as the one described in en WO 2005/093015 A1.

The glycerol formal esters of the fatty acids show good properties as biofuels. For example, the biofuels obtained by the transesterification of rapeseed oil have a high cetane number, 60.7, which improves the performances of the biofuel in the engine (as shown in Example 1). Furthermore, the biofuel is biodegradable and has a high mass percentage derived from the renewable raw materials.

An advantage of the invention is that new biofuel compositions can be prepared by combining glycerol formal esters with glycerol formal, biodiesel (i.e. methyl or ethyl fatty acid esters), petrol-derived diesel, or mixtures thereof. Therefore, it is possible to prepare binary, ternary, and even quaternary mixtures containing a high proportion of glycerol formal esters.

In case of binary mixtures, the glycerol formal esters may be mixed in any proportion with glycerol formal, biodiesel, or petrol-derived diesel. In this case, the resulting biofuel formulation will benefit from the unique properties of the glycerol formal ester derivatives: on one hand, they are characterised by a high glycerol content; on the other hand, the cetane number is improved.

In case of ternary mixtures, the glycerol formal esters allow glycerol formal to be soluble in methyl or ethyl fatty acid esters (biodiesel) when added to a binary mixture even when the glycerol formal is in a proportion of 20% or higher.

In a preferred embodiment, the process of the invention further comprises mixing the biofuel obtainable either by the transesterification process or by the fat splitting process, as defined above, with a compound selected from the following group: glycerol formal, biodiesel, petrol-derived diesel, and mixtures thereof.

Preferably, the biodiesel are methyl or ethyl esters from the transesterification process of rapeseed, sunflower, palm, coconut, soy, olive oils, and mixtures thereof.

A second aspect of the present invention refers to the biofuel obtainable by the process as defined above.

In a preferred embodiment, the biofuel formulations comprise about 70-85% of the biofuel obtainable either by the transesterification process or by the hydrolysis process, as defined above, and about 15-30% of glycerol formal.

In another preferred embodiment, the biofuel formulation comprises a proportion of glycerol formal equal or higher than 12%; and a proportion of the biofuel obtainable either by the transesterification process or by the hydrolysis process, as defined above, equal or higher than 39%; being the rest, up to 100%, biodiesel obtained from rapeseed oil.

In another preferred embodiment, the biofuel formulation comprises a proportion of glycerol formal equal or higher than 12%; and a proportion of the biofuel obtainable either by the transesterification process or by the hydrolysis process, as defined above, equal or higher than 40%; being the rest, up to 100%, biodiesel obtained from sunflower oil.

In another preferred embodiment, the biofuel formulation comprises a proportion of glycerol formal equal or higher than 19%; and a proportion of the biofuel obtainable either by the transesterification process or by the hydrolysis process, as defined above, equal or higher than 7%; being the rest up to 100% biodiesel obtained from palm oil.

In another preferred embodiment, the above-mentioned biofuel formulations include a proportion of petrol-derived diesel of about 50-95%. In still a more preferred embodiment, the proportion of petrol-derived diesel is 55-75%.

The biofuel of the present invention can also contain one or more additional components selected from antioxidants, agents for increasing the octane number, biocides, chelating agents, detergents, dispersants, solvents, corrosion inhibitors, oxide inhibitors, and cetane improvers.

A third aspect of the present invention refers to the use of the products of the present invention as biofuels.

Throughout the description and claims the word "comprise" and variations of the word, such as "comprising", is not intended to exclude other technical features, additives, components, or steps. Additional objects, advantages and features of the invention will become apparent to those skilled in the art upon examination of the description or may be learned by practice of the invention. The following examples and drawings are provided by way of illustration, and is not intended to be limiting of the present invention.

EXAMPLES

Example 1

Preparation of Glycerol Formal Esters from Fatty Acid by Transesterification of Rapeseed Oil with Glycerol Formal A glycerol formal solution (3557.4 g, 34.2 mol) and sodium hydroxide (14.3 g, 0.21 mol) are added to rapeseed oil (262.5 g, 0.28 mmol). The mixture is heated up to 70° C. and stirred at 250 rpm for 16 hours. Subsequently, the mixture is cooled down to 30° C. and water was added to the crude reaction until the total separation of the two layers. The polar layer was neutralised to pH 7 and the excess of glycerol formal is distilled at reduced pressure to be recycled. The fraction which is not distilled and which contains free glycerol is reacted with formaldehyde in the presence of an acid catalyst to regenerated the glycerol formal. The apolar layer (the upper layer), which contains glycerol formal ester, is separated and washed with an aqueous solution of $H_2SO_4$ 5% (312.3 ml). After that, the organic layer is washed with water until the pH is 7. The product is dried with anhydrous $Na_2SO_4$, filtered off and finally, the residual water was distilled off at reduced pressure yielding 254 g of the title compound. Yield 98%. The product is a transparent yellowish liquid. $^1$H-NMR (CDCl$_3$, 400 MHz): δ 0.87 (t, 3H, CH$_2$CH$_3$), 1.29 (m, 17.3H, CH$_2$), 1.63 (m, 2H, CH$_2$CH$_2$CH$_2$CO), 2.02 (m, 2H, CH$_2$CH$_2$CH=CH), 2.36 (t, 2H, CH$_2$CH$_2$CO), 2.77 (m, 0.86H, CH=CHCH$_2$CH=CH), 5.025-3.65 (m, 7H, acetal) y 5.33 (m, 2.83H, CH=CH).

TABLE 1

Properties as biofuel of the glycerol formal ester of rapeseed oil.

| Parameter | Method | Result | Unid |
|---|---|---|---|
| Density at 15° C. | DIN EN ISO 12185 | 954 | kg/m³ |
| Flash Point | DIN EN ISO 3679 | 226 | ° C. |
| Carbon residue (10%) | DIN EN ISO 10370 | 0.07 | % (p/p) |
| Cetane Number | IP 498 | 60.7 | — |

Example 2

Preparation of Mixtures of Fatty Acid Esters/Glycerol Formal and Miscibility Evaluation The miscibility of glycerol formal when mixed with a biodiesel fuel derived from rapeseed, sunflower or palm oil in a 20% proportion (w/w) are compared in Table 2 for two different temperatures.

TABLE 2

Miscibility of the mixtures biofuel/glycerol formal (80/20)

| Biofuel | Temperature (° C.) | Miscible |
|---|---|---|
| Glycerol formal esters of rapeseed oil fatty acid. | 0 | Yes |
| | 20 | yes |
| Methyl ester of fatty acid of rapeseed oil. | 0 | No |
| | 20 | No |
| Methyl ester of fatty acid of sunflower oil. | 0 | No |
| | 20 | No |
| Methyl ester of fatty acid of palm oil. | 0 | Solidify at 17° C. |
| | 20 | No |

Example 3

Preparation of Mixtures of Methyl Fatty Ester/Glycerol Formal/Glycerol Formal Ester of Fatty Acid of Rapeseed Oil and Evaluation of the Miscibility The miscibility of the ternary mixture biodiesel/glycerol formal/glycerol formal ester has been evaluated with different sources of fatty acids at different temperatures. The results are outlined on Table 3.

TABLE 3

Miscibility of the mixtures biodiesel/glycerol formal/glycerol formal from rapeseed oil fatty acid.

| Fatty acid | Methyl fatty ester | Glycerol Formal | Glycerol formal ester of the fatty acid (rapeseed) | Miscible | |
|---|---|---|---|---|---|
| Nature | % | % | % | 0° C. | 20° C. |
| Rapeseed | 49 | 12 | 39 | SI | SI |
| Sunflower | 48 | 12 | 40 | SI | SI |
| Palm | 73 | 20 | 7 | Solid | SI |

The invention claimed is:

1. A biofuel formulation comprising:
a biofuel component comprising components (I) and (II),

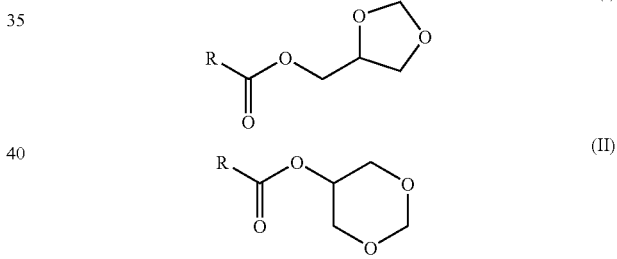

wherein R is an alkyl chain from a fatty acid derived from triglycerides of an oil or fat of animal or vegetable origin, and wherein said biofuel component is mixed with a compound selected from the group consisting of glycerol formal, biodiesel, petro-derived diesel and mixtures thereof.

2. A biofuel formulation according to claim 1, wherein the biodiesel is selected from the group consisting of methyl or ethyl esters from the transesterification of rapeseed oil, sunflower oil, palm oil, coconut oil, soy oil, olive oil, and mixtures thereof.

3. A biofuel formulation according to claim 1, which comprises about 70-85% of said biofuel component and about 15-30% of glycerol formal.

4. A biofuel formulation according to claim 1, which comprises a proportion of glycerol formal equal or higher than 12% and a proportion of said biofuel component equal or higher than 39%, being the rest, up to 100% of the mixture, biodiesel from rape-seed oil.

5. A biofuel formulation according to claim 1, which comprises a proportion of glycerol formal equal or higher than 12%, and a proportion of said biofuel component equal or higher than 40%, being the rest, up to 100% of the mixture, biodiesel obtained from sunflower oil.

6. A biofuel formulation according to claim 1, which comprises a proportion of glycerol formal equal or higher than 19%, and a proportion of said biofuel component equal or higher than 7%, being the rest, up to 100% of the mixture, the biodiesel obtained from palm oil.

7. A biofuel formulation according to claim 1, which comprises a proportion of petrol-derived diesel about 50-95%.

8. A biofuel formulation according to claim 1, which further comprises one or more additional components selected from the group consisting of: antioxidants, agents for increasing the octane number, biocides, chelating agents, detergents, dispersants, solvents, corrosion inhibitors, oxide inhibitors, and cetane improvers.

* * * * *